US007706865B1

(12) United States Patent
Snell

(10) Patent No.: US 7,706,865 B1
(45) Date of Patent: Apr. 27, 2010

(54) APPARATUS AND METHOD FOR CARDIAC RHYTHM DETECTION

(75) Inventor: Jeffery D. Snell, Chatsworth, CA (US)

(73) Assignee: Pacesetter, Inc., Sylmar, CA (US)

( * ) Notice: Subject to any disclaimer, the term of this patent is extended or adjusted under 35 U.S.C. 154(b) by 360 days.

(21) Appl. No.: 11/626,754

(22) Filed: Jan. 24, 2007

(51) Int. Cl.
*A61B 5/04* (2006.01)

(52) U.S. Cl. ..................................... 600/509

(58) Field of Classification Search ................. 600/509; 607/4, 9, 17, 15, 25, 5, 8
See application file for complete search history.

(56) References Cited

U.S. PATENT DOCUMENTS

| 5,653,738 | A | * | 8/1997 | Sholder ........................ 607/14 |
| 5,720,295 | A | | 2/1998 | Greenhut et al. |
| 5,810,739 | A | | 9/1998 | Bornzin et al. |
| 6,029,087 | A | | 2/2000 | Wohlgemuth |
| 6,101,416 | A | | 8/2000 | Sloman |
| 6,493,584 | B1 | * | 12/2002 | Lu ................................. 607/9 |
| 6,654,637 | B2 | | 11/2003 | Rouw et al. |
| 6,731,980 | B1 | * | 5/2004 | Mouchawar et al. ........... 607/9 |
| 7,254,441 | B2 | * | 8/2007 | Stroebel ......................... 607/9 |
| 2001/0016693 | A1 | | 8/2001 | Bonnet et al. |
| 2002/0183640 | A1 | | 12/2002 | Bjorling |
| 2007/0066999 | A1 | * | 3/2007 | White ............................ 607/9 |
| 2007/0135864 | A1 | | 6/2007 | Gunderson et al. |

* cited by examiner

*Primary Examiner*—George Manuel
*Assistant Examiner*—Robert N Wieland

(57) ABSTRACT

Cardiac pacing may be controlled through retrospective detection of events that are sensed during a given period of time. In some embodiments a detection decision is made substantially prior to the end of an escape interval. In some embodiments the mode of detection may be changed near the end of the period of time. In some embodiments the period of time is extended when an event is detected near the end of the period of time.

20 Claims, 10 Drawing Sheets

APPARATUS AND METHOD FOR CARDIAC RHYTHM DETECTION

TECHNICAL FIELD

This application relates generally to implantable cardiac stimulation devices and, more specifically, to a stimulation apparatus or method that delays characterizing a sensed event for a period of time after the event was sensed.

BACKGROUND

Implantable medical devices, such as pacemakers, defibrillators, and cardioverters (which may collectively be referred to herein as implantable cardiac stimulation devices), are designed to monitor and stimulate the heart of a patient that suffers from a cardiac arrhythmia. Using leads connected to a patient's heart, these devices typically stimulate the cardiac muscles by delivering electrical pulses in response to measured cardiac events that are indicative of a cardiac arrhythmia. Properly administered therapeutic electrical pulses may successfully reestablish or maintain the heart's regular rhythm.

In a healthy heart, contractions occur first in the muscles associated with the atrial chambers of the heart, followed by contractions in the muscles associated with the larger ventricular chambers of the heart. In this way, the atria assist in the filling of the ventricular chambers with blood returning from the veins. This increases the end-diastolic volume thereby increasing the stroke volume to enable the ventricles to more efficiently pump blood to the arteries.

Given the interaction of these chambers, efficient operation of the heart is predicated on each of the chambers operating in a proper timing sequence and having contractions that pump a sufficient amount of blood from the chamber. For example, during contraction the right atrium should pump enough blood to optimally "fill" the right ventricle chamber. Moreover, this should occur immediately before the right ventricle begins to contract. In this way, the heart may efficiently pump blood on a repetitive basis.

A healthy heart repetitively contracts in the above described manner in response to the generation and conduction of electrical signals in the heart. These electrical signals are generated in and conducted through the heart during every beat of the heart. A simplified example of these cardiac signals follows.

Activity for a given beat begins with the generation of a signal in a sinus node of the heart. This signal causes contraction to begin first in the atria. The signal from the sinus node propagates via a conduction system to an atrioventricular ("A-V") node. The signal is inherently delayed for a short period of time (usually less than 200 ms) within the AV node allowing the atria to contract to help to fill the ventricles. The signal then propagates from the A-V node through the bundle of His to the left and right ventricles via a specialized conduction system. Contraction in each ventricle commences in a coordinated manner when the signal "reaches" the respective muscle fibers in the ventricle.

In an attempt to maintain regular contractions in an unhealthy heart a typical stimulation device may track the type and timing of the signals generated by the heart. In this way the stimulation device may determine whether cardiac events (e.g., contractions) are occurring and whether they are occurring at the proper times. In the event contractions are not occurring or are occurring at undesirable times, the stimulation device may deliver electrical pulses to one or more of the chambers of the heart in an attempt to initiate the desired contractions at the desired times.

A typical stimulation device may track cardiac signals through the use of leads that are implanted in one or more of the chambers of the heart. Through the use of amplification, threshold detection and filtering, signals received via the leads may be associated with the cardiac events discussed above. Conventionally, these cardiac events may be referred to as P-waves, R-waves, T-waves, etc. Here, a P-wave corresponds to a contraction (depolarization) of an atrium. An R-wave corresponds to a contraction (depolarization) of a ventricle. A T-wave corresponds to a return to a resting state (repolarization) of a ventricle.

Conventionally, these events have been sensed and characterized in real-time. For example, implantable devices which detect the cardiac rhythm, e.g., spontaneous atrial contractions (or P-waves) and spontaneous ventricular contractions (or R-waves with or without a preceding atrial event), generally utilize the same basic structure for this function: 1) a sense amplifier feeding a threshold detector for cardiac event detection; 2) a refractory period followed by an alert period to qualify the output of the threshold detector; 3) a trigger signal out of the threshold detector during the alert period identifies a P-wave or R-wave; and 4) no trigger signal out of the threshold detector during the alert period results in a pacing pulse at the end of the alert period.

The sense amplifier may include or be associated with a signal filter. Here, a bandwidth of the filter may be selected to allow the signals that the system is attempting to detect to pass through the filter. Ideally, the filter will reject any other signals. That is, these other signals may not pass through the filter or may be significantly attenuated by the filter.

Any signals that pass through the filter may then be provided to the threshold detector. The threshold detector will generate an output signal in the event the amplitude of the signal exceeds a predefined threshold level. The output signal is thus taken as an indication that a certain cardiac event (e.g., an atrial or a ventricular contraction) has occurred.

By analyzing the type and timing of these indications the stimulation device may determine whether stimulation pulses need to be generated. Thus, if the stimulation device detects cardiac events at the appropriate relative times, the stimulation device may simply continue monitoring the received indications. On the other hand, if an indication has not been received for a predefined period of time, the stimulation device may deliver an appropriate stimulation (e.g., pacing) pulse to the heart.

Immediately after pacing or sensing, a blanking period (or refractory period) may be used to block the threshold detector output, preventing redetection of the event or detection of the depolarization created by the pacing pulse. Typically, the latter part of this refractory period includes a type of noise detection which acts to extend the blanking until the input signal has been quiet for some minimal time interval.

At the end of the blanking/refractory period the alert period begins. During the alert period, any signal that exceeds a programmed detection threshold (e.g., a second input to the threshold detector) causes a signal or interrupt to the stimulation device thereby signaling a detection of a cardiac event.

In practice, the above techniques may not always provide a proper indication of cardiac events. For example, very little information about the true nature of a detected event may be available at the point of detection of the typical P-wave or R-wave since the detection may occur close to the leading edge of the event. Moreover, P-wave detection is dependent on the bandpass characteristics of the sense amplifier and the timing of the alert period. As a result, a P-wave detection may identify a true P-wave in some instances and, in other instances, may identify a far-field R-wave, a far-field T-wave, extracardiac physiologic noise or external noise (from electrocautery, anti-theft systems, etc.). Similarly, an R-wave detection may signal the start of an R-wave in some instances and, in other instances, may identify a T-wave, redetection of the same R-wave, or noise as described previously for P-wave detection.

Various techniques have been developed in an attempt to improve the accuracy of the characterization of cardiac events. For example, post-ventricular atrial blanking ("PVAB") may act as a parallel refractory period for AF detection. Pre-ventricular atrial blanking ("PREVAB") may improve far-field R-wave discrimination. Morphology discrimination (e.g., characterizing the shape of a waveform) may be used in an attempt to classify a signal after is has been detected.

The use of these techniques, however, may not guarantee that a stimulation device will provide an accurate indication of all cardiac events. Accordingly a need exists for more effective techniques for identifying cardiac activity.

SUMMARY

This application relates to a stimulation apparatus or method that may retrospectively characterize sensed cardiac events. The apparatus or method may then adjust timing and/or apply therapy in accordance with the characterized events. For convenience, an embodiment of an apparatus constructed or a method practiced according to the invention may be referred to herein simply as an "embodiment."

In some embodiments, an event may not be characterized immediately after it has been sensed by a stimulation device (e.g., after an output signal is generated by a threshold detector). For example, the apparatus or method may continue sensing operations for a given period of time.

In some embodiments, the characterization is applied to events sensed in an atrial channel. For example, after an event is sensed it may be preliminarily characterized as a P-wave. However, sensing operations in the atrial channel may continue for a period of time. Once the period of time elapses, a determination may then be made as to whether the initial event was a P-wave.

In some embodiments the period of time ends near the end of an escape interval. For example, any events from the atrial channel may be characterized immediately before a decision needs to be made as to whether to pace the atrium.

The characterization of any sensed events may be accomplished using a variety of techniques. In some embodiments these techniques may include one or more of morphology analysis, frequency analysis, timing analysis, correlation analysis, etc. In addition, other information from other channels may be used to characterize the sensed events. Signals from such other channels may include, for example, far-field signals, patient activity signals, cardiac sound signals, wideband IEGM signals, alternate sensing vector signals, pressure signals, impedance signals and respiration signals. In some instances more than one event may be sensed in an input channel (e.g., the atrial channel) during the period of time. Here, a decision may be made as to which, if any, of the sensed events is, for example, a P-wave.

Once the sensed signal or signals have been characterized, cardiac pacing may be adjusted accordingly. For example, once a decision is made as to whether a particular event has been detected or that no expected events have been detected, the pacing intervals of the system may be maintained or modified. In addition, a decision may be made to apply a stimulation pulse.

In some embodiments the mode of detection may be changed near the end of an escape interval. For example, the mode of detection may be changed from a retrospective mode to a real-time mode (e.g., threshold detection). In this way, a decision as to whether an event (e.g., a P-wave) has been detected may be made more quickly. Hence, such a decision may be made, for example, before the escape interval expires.

In some embodiments the end of the period of time may be extended when an event is sensed or detected near the end of an escape interval. In this way, unnecessary pacing may be avoided if it is determined, for example, that an atrial contraction has occurred. Moreover, the extended time period may enable the stimulation device to more fully analyze the late arriving event and/or analyze the event in its entirety.

In some embodiments the period of time corresponds to a window of time that commences when an event is initially sensed. For example, the first event sensed or detected in the atrial channel after the refractory period ends may define the start of the window.

In some embodiments the period of time corresponds to a window of time that ends when an event is sensed. For example, a detection of an R-wave may define the end of the window.

BRIEF DESCRIPTION OF THE DRAWINGS

These and other features, aspects and advantages of the invention will be more fully understood when considered with respect to the following detailed description, appended claims and accompanying drawings, wherein:

Figure 1:
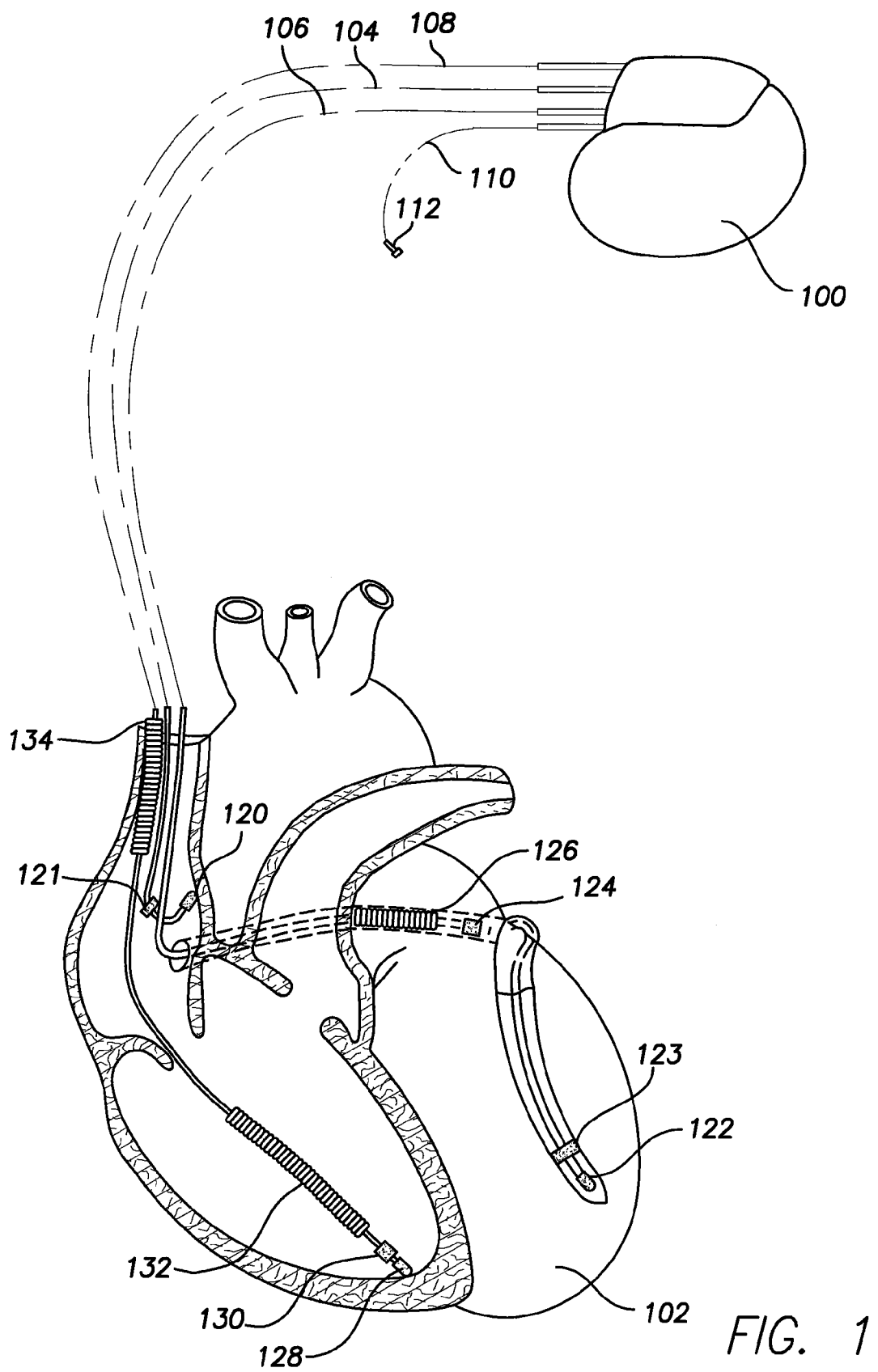
FIG. 1 is a simplified diagram of one embodiment of an implantable stimulation device in electrical communication with at least three leads implanted in a patient's heart for delivering multi-chamber stimulation and shock therapy in accordance with the invention.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

Exemplary Stimulation Device

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left ventricular ring electrode 123, left atrial pacing therapy using at least a left atrial ring electrode 124, and shocking therapy using at least a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

In some embodiments, the stimulation device 100 may receive signals from one or more other leads (e.g., lead(s) 110) and sensors (e.g., sensor(s) 112). These leads and sensors may be implanted in the heart or at other locations in a patient. These leads and sensors may be used to sense a variety of signals including, for example, far-field signals, patient activity signals, cardiac sound signals, wideband IEGM signals, alternate sensing vector signals, pressure signals, impedance signals and respiration signals.

Figure 2:
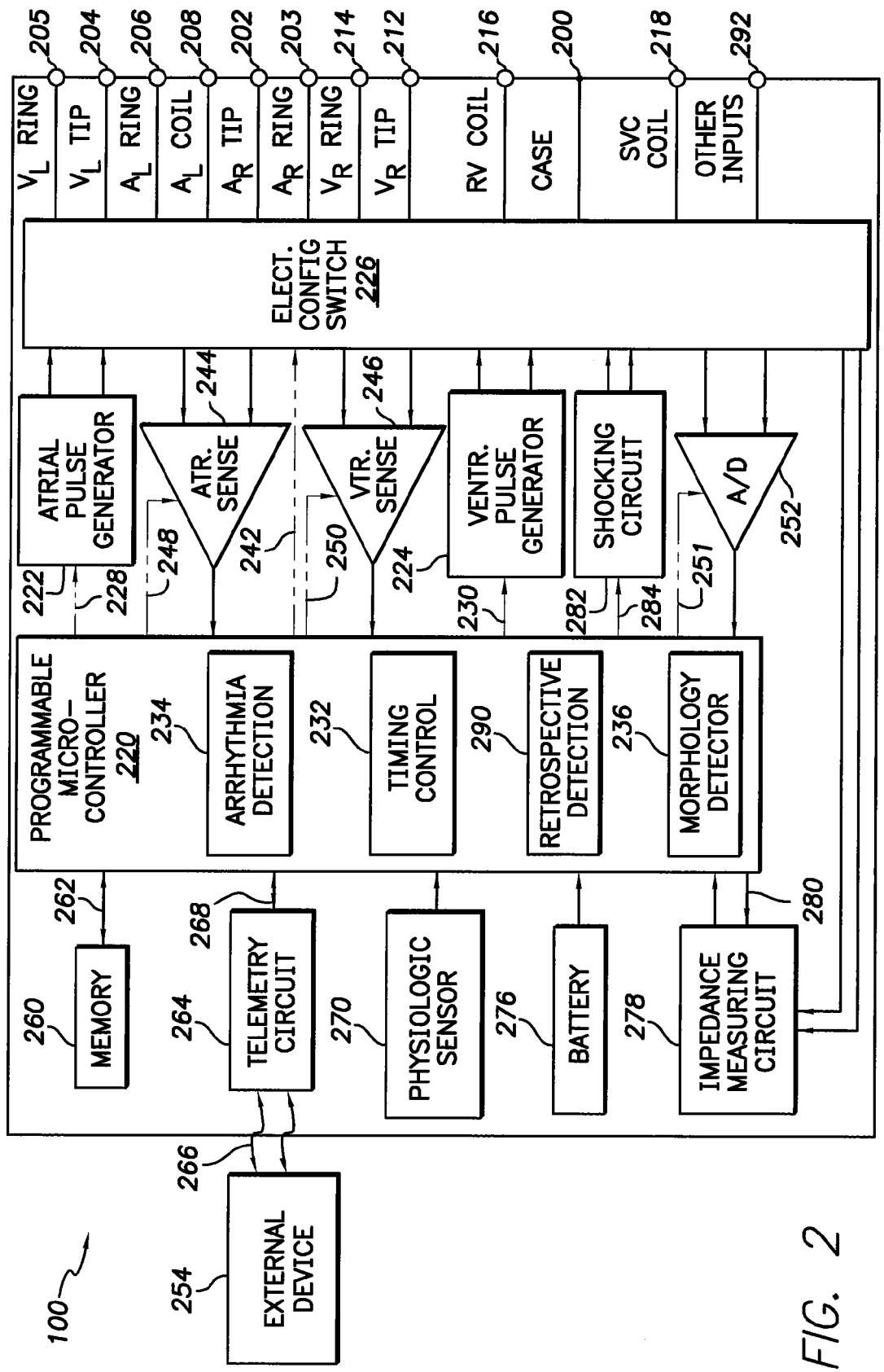
FIG. 2 is a simplified functional block diagram of one embodiment of a multi-chamber implantable stimulation device constructed in accordance with the invention, illustrating basic elements that are configured to provide cardioversion, defibrillation or pacing stimulation or any combination thereof.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes at least a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

In some embodiments, the connector may include one or more terminals (e.g., terminal 292) for receiving signals from other input leads and sensors. For example, the terminal(s) 292 may be used for receiving signals such a those discussed above in conjunction with lead(s) 110 and sensor(s) 112.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

In some embodiments a retrospective detection circuit 290 may operate in conjunction with the timing control circuitry 232. The retrospective detection circuit 290 may be used to retrospectively process/analyze received signals to more accurately characterize the corresponding events. In this way, more effective control of the timing of the stimulation pulses may be provided.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals or other signals (e.g., from terminal(s) 292) also may be applied to inputs of an analog-to-digital (A/D) data acquisition system 252. The data acquisition system 252 is configured (e.g., via signal line 251) to acquire intracardiac electrogram or other signals, convert the raw analog data into a digital signal, and store the digital signals for later processing and/or telemetric transmission to an external device 254. In some embodiments, the data acquisition system 252 is coupled to the right atrial lead 104, the coronary sinus lead 106, the right ventricular lead 108 and the other lead(s) 110 through the switch 226 to sample cardiac signals and other signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
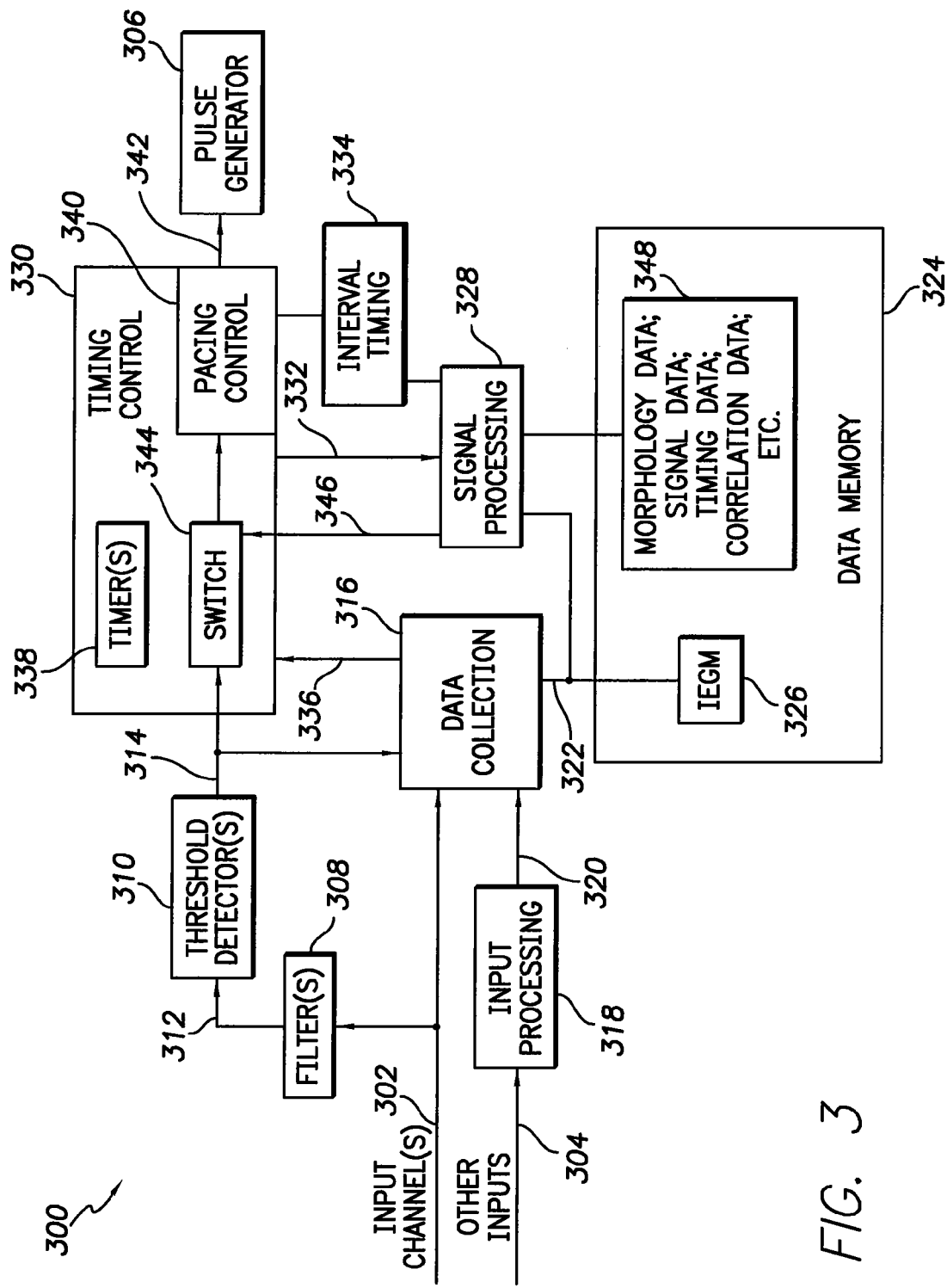
FIG. 3 is a simplified block diagram of one embodiment of a stimulation device constructed in accordance with the invention.

FIG. 3 illustrates one embodiment of a stimulation device 300 that may be configured to provide retrospective detection to control cardiac pacing operations. To reduce the complexity of FIG. 3, only a portion of the components of the stimulation device 300 are illustrated.

The stimulation device 300 processes signals received in one or more cardiac input channels 302 (e.g., one or more atrial and/or ventricular channels) and, optionally, signals received from other inputs 304 to control one or more pulse generators 306. The signals for the input channel(s) 302 may sensed by one or more leads implanted in the left/right atrium/ventricle as discussed above or from other sensing structures. The signals from the other input(s) 304 may be generated by, for example, one or more other cardiac leads, the sensors discussed above in conjunction with FIG. 2 or other sensing structures. The pulse generator(s) 306 may be configured to deliver stimulation pulses to one or more leads implanted in the heart to deliver stimulation pulses to one or more areas of the heart (e.g., right atrium, left atrium, right ventricle, left ventricle, etc.) as discussed herein.

Signals received via the input channel(s) 302 and other inputs 304 may be pre-processed. For example, one or more filters (and associated amplification) 308 and one or more threshold detectors 310 may be configured to detect a particular type of cardiac wave (e.g., a P-wave) received via the input channel 302. The output of the filter(s) and/or threshold detector(s) (e.g., signals 312 and 314) may be provided to a data collection component 316. An input processing component 318 may include filter(s), threshold detector(s) and other circuits for the other inputs 304. The input signals 304 and the output(s) 320 of the input processing component circuits also may be provided to the data collection component 316. The above pre-processing operations may be implemented and performed, for example, as described herein in conjunction with FIG. 2.

The data collection component 316 may store collected data 322 in one or more data memories (e.g., data memory 324). To this end, the data collection component 316 may include analog-to-digital circuitry as discussed herein for converting received analog signals (e.g., signals 302, 320, 314) to digital form. For signals received from cardiac electrodes, the stored data may take the form of, for example, an intracardiac electrogram ("IEGM") 326.

A signal processing component 328 may process the digital data 322 generated by the data collection component 316 to control cardiac pacing operations. Here, the signal processing component 328 may process the digital data 322 as it is generated by the data collection component 312 (e.g., in real-time) or may process digital data (e.g., IEGM 326) retrieved from the data memory 324.

In some embodiments, the signal processing component 328 performs retrospective detection operations in an attempt to more accurately characterize any events associated with the signals received from the inputs 302 and/or 304. For example, the signal processing component 328 may analyze data that was received from an input over a period of time. Based on the data collected throughout the time period, the signal processing component 328 may make a determination as to the nature of the sensed events. For example, the signal processing may characterize the sensed event or events as P-waves, noise, far-field waves, etc.

Received signals may be sensed and/or processed at various times. For example, in some embodiments these operations may be performed periodically. Alternatively, the sensing operations may be performed continuously.

In some embodiments the period of time over which the signal processing component 328 analyzes data (e.g., IEGM 326) is controlled by a timing control component 330. For example, the timing control component 330 may generate or pass through one or more signals 332 that signal when the analysis begins and/or ends. Alternatively, the timing control component 330 may define a window of time that defines the time period over which the digital data (e.g., IEGM 326) is to be processed. In some embodiments the period of time used by the signal processing component 328 may be based on cardiac interval timing values 334. The values 334 may be stored, for example, in registers or the data memory 324.

In some embodiments the data collection component 316 may be configured to collect data over a specified period of time. For example, the timing control component 330 may provide timing signals 336 that indicate when data is to be collected for the retrospective detection operations. In this case, the data collected over the specified period of time may be provided to the signal processing component 328 for analysis.

The timing control component 330 includes one or more timers 338 that generate timing signals and/or data. Based on this timing information or other input signals, the timing control component 330 may generate timing signals or data (e.g., signals 332 and/or 336) to control other timing operations in the device 300. The timing control component 330 may control cardiac timing as discussed above in conjunction with timing control circuitry 232 by defining and maintaining the interval timing values 334.

The other input signals that the timing control component 330 may use for the timing operations may include, for example, signals from real-time detectors (e.g., signals 314 from threshold detector(s) 310). In addition, digital data 322 may be provided (e.g., via component 328) to the timing control component 330 for the timing operations.

The timing control component 330 may include a pacing control component 340 that controls the operation of the pulse generator 306. For example, the pacing control component 340 may generate signals 342 that initiate the generation of stimulation pulses based on the interval timing values 334. Alternatively, the interval timing values 334 may be directly provided to the pulse generator 306. The pacing control component 340 also may maintain the interval timing values 334 by, for example, updating the values 334 based on the signals received via the input 302 and/or 304.

In some embodiments, the timing control component 330 includes a switch or similar functionality 344 that may control whether pacing timing is based on real-time detection signals (e.g., signal 314) or signals 346 from the signal processing component 328. Here, the signals 346 may provide information related to the type and timing of events characterized by the signal processing component 328.

The signal processing component 328 may characterize sensed events using one or more of a variety of techniques. In some embodiments the signal processing component 328 may characterize an event based on the characteristics and/or timing of the corresponding signal. To this end, the signal processing component 328 may perform one or more of morphology processing, correlation processing, timing analysis, frequency analysis and other processing techniques that may assist in characterizing an event.

The characteristics of a received signal may be compared with other known or expected characteristics. To this end, the signal processing component 328 may store and/or use corresponding information 348 stored in the data memory.

In some embodiments timing analysis may involve comparing the time at which an event was sensed with known or expected beat timing. For example, assuming a sensed event is characterized as a P-wave, the R-wave to T-wave ("R-T") interval and the R-wave to P-wave ("R-P") interval may be calculated for that wave based on other sensed events. These intervals may then be compared to known or expected R-T and R-P intervals, respectively. The decision to characterize the event may then be weighted depending on how well the intervals match. In some embodiments the mean and average deviation of the intervals may be stored in the data memory. In this case, a detection may only be indicated for events that fall within such a range. It should be appreciated, however, that other criteria may be used to determine whether the timing interval of an event sufficiently corresponds to a known or expected interval.

In some embodiments a waveform may be characterized using an ensemble averaging scheme. For example, each new point in a digitized waveform (e.g., for a P-wave) may be averaged in a running average. As a result, a collection of data may be acquired for each point in time. From this an ensemble average may be calculated that is a representation of an average P-wave. This representation may then be compared (e.g., on a point-by-point basis) with any candidate P-waves. The absolute values of the differences may then be summed to obtain an absolute point difference. When the resulting average is small, (e.g., within a predefined range) the candidate P-wave may be designated as a true P-wave.

In some embodiments a waveform may be characterized using a correlation scheme such as Kendall's Tau. Briefly, such a scheme may be advantageous because it is effectively amplitude independent. As a result, this scheme may not be affected by respiratory modulation that that be induced on sensed cardiac signals. In general, the scheme involves looking at the relation of every point to every other point (in a forward direction). The relationship to each point is assigned a value (e.g., +1 or −1) depending on the relative amplitude of the points. These values are then combined to provide a correlation value associated with the waveform.

In some embodiments a waveform may be characterized using an approximation of Kendall's Tau. Briefly, this approach avoids calculating square roots by approximating the square roots. In addition, rather than considering every point, only a subset of the points may be processed. An approximation of Kendall's Tau is described, for example, in "Numerical Recipes in C," Second Edition, Cambridge Press, 2002, pages 642-643.

Information (e.g., morphology templates, ensemble averages, correlation data, etc.) used for characterization schemes may be measured/collected and loaded into the stimulation device. For example, tests may be run in a clinical setting and the resulting data downloaded into the stimulation device for later comparison with candidate signals.

Figure 4:
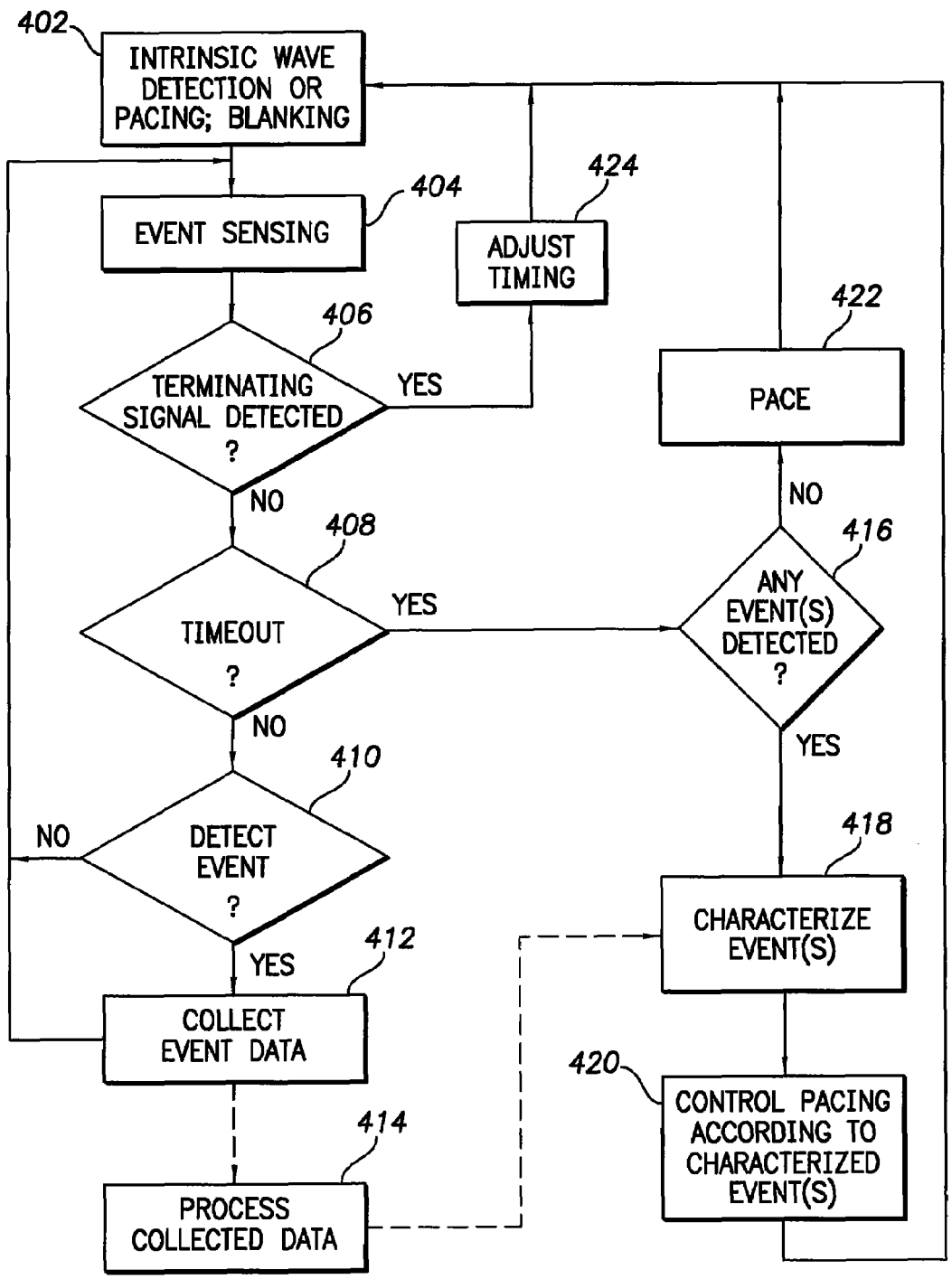
FIG. 4 is a simplified flow chart of one embodiment of retrospective detection operations that may be performed in accordance with the invention.

Referring now to FIGS. 4-8, several examples of operations that may used to control cardiac pacing based on retrospective detection will be described. FIG. 4 is a simplified flowchart of operations that may be performed each beat to control cardiac timing. Through the use of operations such as those described, retrospective detection may be used to control pacing on a beat-by-beat basis.

In some embodiments, the process of FIG. 4 may be performed for the atrial phase of a beat cycle and/or the ventricle phase of the beat cycle. For example, the process may sense for a P-wave in an atrial channel. If a P-wave is not sensed before the end of the atrial escape interval the process may pace an atrium (or atria) or some other appropriate location in the heart. The process also may sense for an R-wave in a ventricular channel. Here, if an R-wave is not sensed before the end of the corresponding escape interval the process may pace a ventricle (or ventricles) or some other appropriate location in the heart.

As represented by block 402, a cycle may begin after an intrinsic cardiac contraction is detected (e.g., a P-wave or an R-wave) or after a pacing pulse (e.g., in an atrium or a ventricle) is applied to the heart. A blanking interval follows the detection or pacing to prevent, for example, re-detection of the detected event or detection of the pulse. The blanking period is followed by an alert period during which the stimulation device may sense one or more input channels to determine if and when any intrinsic contractions occur. As mentioned above, based on the timing of the detection/pulse, an escape interval defines a maximum period of time the stimulation device waits before applying a pacing pulse. In other words, if a particular intrinsic event (e.g., a P-wave or R-wave) is not detected before the end of the escape interval, the stimulation device stimulates the appropriate area (e.g., atrium, ventricle, etc.) of the heart.

As represented by blocks 404-412, after the blanking period ends, the stimulation device senses for events in one or more input channels for a period of time. Depending on the particular application, this may involve sensing for signals generated in one or more areas (e.g., atrium or ventricle) of the heart (block 404).

In some embodiments, an event sensed in another channel may serve as an indication that the sensing of blocks 404-412 should terminate (block 406). For example, when sensing in an atrial channel, a detection of an R-wave (e.g., in a ventricle channel) may cause the system to exit the loop and adjust the interval timing according to the time of the R-wave (block 424). Here, it may be the case that any event sensed in the atrial channel was not a P-wave given the expected relative timing of P-waves and R-waves. When sensing in an atrial channel, the process may return to block 402 since an R-wave was detected.

In some embodiments, a decision may not be made immediately upon detection of an R-wave. For example, the process may continue to sense and process signals from the channel(s) to ensure that the event was a true R-wave and not a wave such as a premature ventricular contraction ("PVC"). Accordingly, all of the signal data associated with the R-wave (e.g., the entire R-wave) may be further analyzed (e.g., using morphology-based discrimination). In addition, other events sensed via the channels may be analyzed to determine whether they more closely match a true R-wave. The timing of other events also may be analyzed to determine which of the signals is a true R-wave based on the relative timing of the events. For example, if the event was a PVC, it may be unlikely that a true P-wave would have been sensed in the atrial channel.

A decision as to the true nature of a candidate R-wave may be delayed, for example, until a decision needs to be made as to whether to pace the ventricles. For example, if the candidate R-wave is received 200 mS before the end of the A-V interval, data may be collected for, for example, 150-200 mS after the candidate R-wave was detected.

As represented by block 408, the sensing operations of blocks 404-410 may continue for a prescribed period of time. In some embodiments this period of time may be related to the escape interval. For example, these operations may continue until the end of the escape interval or some time that is near the end of the escape interval. In a typical application, these operations may terminate prior to the end of the escape interval.

As represented by blocks 410 and 412, the sensing operations continue and, when an event (e.g., in the atrial or ventricular channel) is detected, data associated with the sensed event may be collected. In some embodiments data collection may commence after the first event has been detected in an input channel. Hence, the data collection process may be defined in terms of a triggered window where the window commences with a first detected or sensed event. The window may then terminate with another detected or sensed event (e.g., block 406) or at a predefined time (e.g., the end of a time period as defined by an escape interval). In some embodiments data collection (block 412) may be performed to collect data associated with a sensed event.

In some embodiments, detection of the first event may be performed using a real-time detector and/or signal processing. For example, the output of the threshold detector 310 (FIG. 3) may be used to signal the first event. Alternatively, data 322 collected in real-time also may be processed in real-time by the signal processing component 328 to generate an indication of the first signal.

In alternative embodiments, data may be collected the entire period of time regardless of whether any events have been sensed in the input channel. Hence, the operation represented by block 410 may be omitted.

The dashed line to block 414 represents that the collected data may be processed during the loop of blocks 404-412 and/or may be processed after the process exits the loop. In the former case, the processing may be performed as the data is collected, after each sensed event is collected, etc.

In either case, the processing is typically configured such that the collected data is characterized before expiration of a period of time. For example, in a typical embodiment a determination is made before expiration of the escape interval as to which type of event is associated with the signal received via the input channel. In this way, a stimulation pulse may be applied to the heart at the appropriate time, if necessary.

As discussed herein, processing of the collected data may comprise a variety of techniques. For example, processing may involve template matching based on amplitudes, zero crossings, waveform correlation, etc.

Processing may involve frequency analysis that is used, for example, to determine the frequency content of the received signals. For example, signals may be passed through one or more filters to provide an indication of whether the signals contain relatively high or relatively low frequency components with respect to one another or a reference signal. In this way, one wave (e.g., a T-wave) may be distinguished from another wave (e.g., a P-wave or an R-wave) based on a lower frequency content. In some embodiments frequency analysis may involve digitally filtering the received signals and performing a fast Fourier analysis ("FFT").

Signals also may be discriminated by using different types of leads to sense signals. For example, signals may be sensed using unipolar electrodes (e.g., tip-to-can) and bipolar electrodes (e.g., tip-to-ring). In this case, the bipolar electrode may, in effect, perform a high pass filter function that may be used to discriminate between different signals.

In some embodiments, different leads may be used to sense far-field signals relating to a given event. These far field signals may then be used to characterize an event. For example, a T-wave of relatively large magnitude may be detected in the ventricles. However, a far-field P-wave typically will not be detected in the ventricles. In addition, if a signal is detected in the atrium and then a similar signal is detected later in time in the ventricles, this may be an indication that the signal was a far-field signal (that tripped the lower threshold of an atrial threshold detector) of some event other than a P-wave.

Processing also may involve analyzing the slew rate(s) of the signals. For example, the slope of a T-wave may be different than the slope of a P-wave.

Analysis of signals in addition to the primary atrial or ventricular bipolar sense signals may be performed. For example, signals resulting from unipolar sensing, wide band IEGM sensing, heart sound sensing, pressure sensing and other sensing may be used to characterize a given sensed event.

In some embodiments the mode of detection may be changed upon detection of an event. For example, the processing may involve initially characterizing a sensed event according to a real-time detection. For example, when a threshold detector for the atrial channel indicates a detection, that event may be characterized as a P-wave candidate. A final decision as to whether that event is a P-wave may not be made, however, until intervention is required (e.g., the end of the escape interval). This provides additional time to sense other events that may be received via that channel. Consequently, it may be determined at the end of the time period that the initially characterized event was a true P-wave or that some other event that was sensed during the time period was the true P-wave.

Referring again to block 408 in FIG. 4, when the end of the time period is reached, the process proceeds to block 416. In some embodiments if no events were sensed during the time period this means that the escape interval has expired with no intrinsic contractions. As a result, the stimulation device paces the heart as necessary (block 422). The process may then proceed back to block 402 for the next phase of the process.

If, at block 416, at least one event was sensed, the process attempts to characterize all the sensed events. As represented by the dashed line to block 418, this characterization is based on the processing of the collected data. Again, the processing may be performed during the time period and/or after the time period ends.

As discussed herein, the process of characterizing a sensed event may include, for example, analyzing the characteristics of the sensed event and, in some cases, comparing these characteristics with known or expected characteristics.

In addition, as discussed herein, this process also may involve analyzing other sensed signals (e.g., pressure, activity, etc.). For example, it may be expected that the timing intervals are shorter when the activity level (rate response) of the patient is high.

Once the sensed event(s) are characterized, the process proceeds to block 420 and the cardiac pacing is controlled as necessary based on the characterization of the sensed event(s). For example, if it is determined that a P-wave was detected, the interval timing may be adjusted (e.g., shifted in time) accordingly. Alternatively, the interval timing may be left unchanged if this is warranted by the timing of the sensed event. In some cases, pacing may be inhibited based on the current phase of the beat cycle as determined from the sensed event. The process may then proceed back to block 402 and the above operations performed for the next portion of the beat cycle (e.g., the ventricle portion) or for the next beat cycle.

Figure 5:
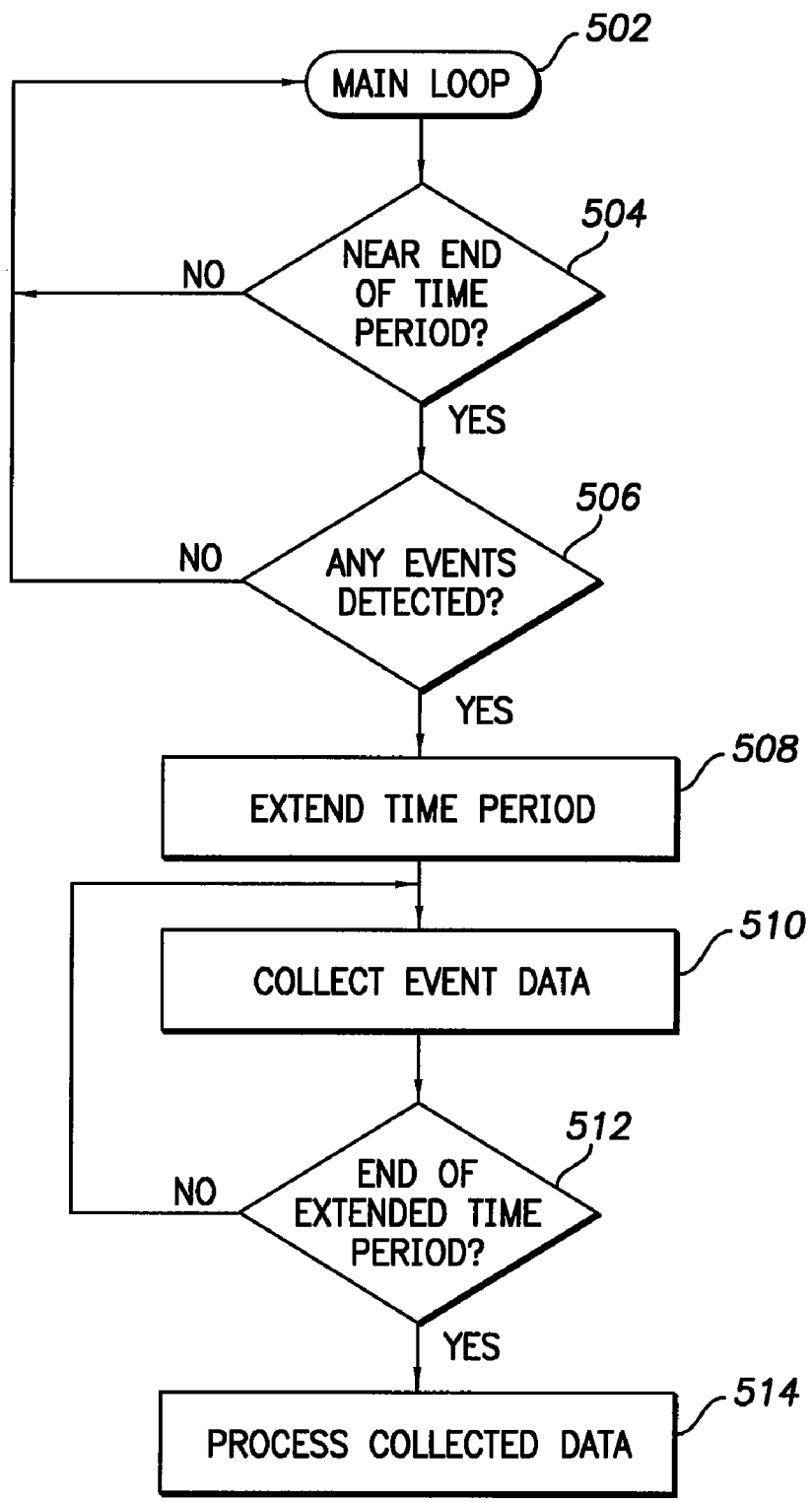
FIG. 5 is a simplified flow chart of one embodiment of retrospective detection operations that may be performed near an end of a time period in accordance with the invention.

FIG. 5 illustrates one embodiment of operations where the time period may be extended when an event is sensed near the end of the time period. As represented by block 502, the operations of FIG. 5 may be incorporated into the loop of FIG. 4, for example, by exiting from the loop and re-entering the loop near block 408.

At block 504 the process determines whether the end of the time period is near. If the process is not near the end of the time period the process returns to the main loop.

In some embodiments near may be defined as an amount of time that is less than the time it takes to process a sensed event and/or to characterize any sensed events. In some embodiments near may be defined as a predefined amount of time or a predefined percentage of the time period. The above times are presented as examples only. Accordingly, it should be understood that other definitions of near may be used in accordance with the teachings herein.

At block 506, the process determines whether any events have been detected near the end of the time period. If no events have been detected the process may, for example, return to the main loop. In this way, the process may continue to sense for events (in the main loop) and will continue to perform the checks at blocks 504 and 506 to determine whether to extend the time period.

On the other hand, when an event has been detected near the end of the time period the time period is extended (block 508). Extension of the time period may be provided, for example, in situations where it is desirable that fusion be avoided even at the cost of some potential cardiac rate reduction.

The length of the time extension may be defined based on various criteria. For example, the extension may be defined as an amount of time it takes to process a sensed event and/or to characterize any sensed events. In this way, the time may be extended only as much as necessary to properly characterize the late arriving sensed event. Alternatively, the extension may be defined as a predefined amount of time or a predefined percentage of the time period. The above times are presented as examples only. Accordingly, it should be understood that other definitions of the extension time may be used in accordance with the teachings herein.

As represented by blocks 510 and 512, data associated with the sensed event is collected, as necessary, until the end of the extended time period. In some embodiments, the collected data also may be processed at least in part during this time interval.

After the extended time period expires, the collected data is processed and characterized. Thus, the process may re-enter the main loop at, for example, block 418. It should be appreciated that the above description is provided as an example. Thus, other criteria may be used to define when the time period may be extended.

Figure 6:
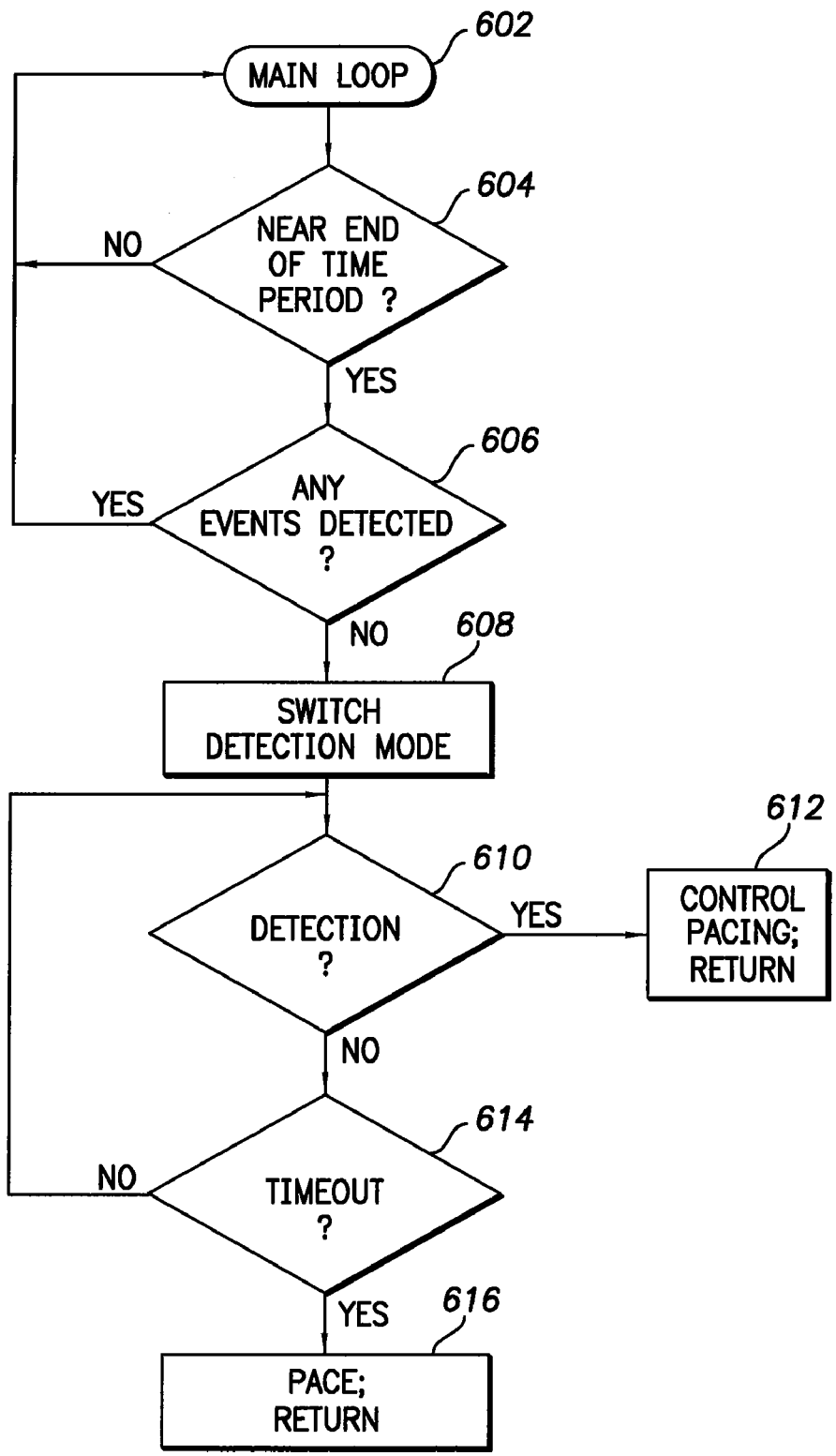
FIG. 6 is a simplified flow chart of one embodiment of retrospective detection operations that may be performed near an end of a time period in accordance with the invention.

FIG. 6 illustrates one embodiment of operations where a mode of detection may be changed near the end of the time period. As represented by block 602, the operations of FIG. 6 may be incorporated into the loop of FIG. 4, for example, by exiting from the loop and re-entering the loop near block 408. In addition, the operations of FIG. 6 may be combined with the operations of FIG. 5 so that near the end of the time period the mode of detection may be changed and the time period may be extended.

At block 604 the process determines whether the end of the time period is near. Here, near may be defined as discussed above or using some other criteria. For example, at block 604 near may be defined as an amount of time necessary to perform a real-time detection (e.g., using a threshold detector). If the process is not near the end of the time period the process returns to the main loop.

In some embodiments, the process may determine whether any events have already been sensed or detected (block 606). This operation may be performed, for example, when the change of mode is only desirable when an event has not already been sensed. This may be the case, for example, when it is advantageous to switch to a real-time mode of detection near the end of the time period so that a detection decision may be made relatively quickly. In this way, a reasonably reliable decision may be made before the end of the escape interval even for a very late arriving sensed event.

In the embodiments including block 606, if an event has been detected the process returns to the main loop. Thus, the process may continue to utilize retrospective detection to characterize the sensed event(s).

Alternatively, it may be advantageous to switch modes even if a prior event has been detected. For example, the process may be configured to analyze all detected events (from all detection modes) at the end of the time period.

At block 608, the process switches the mode of detection. As discussed above, this may involve switching from, for example, a retrospective detection mode to another detection mode. In some embodiments, the new detection mode may be a real-time mode that generates a detection signal using, for example, a threshold detector. It should be appreciated, however, that the above operations may be applicable to detection modes other than those specifically described herein.

As represented by blocks 610 and 614, the new mode of detection is performed until the end of the time period (or extended time period). When an event occurs very close to the end of the escape interval it is possible that fusion may occur with an intrinsic event. This may be an acceptable tradeoff to preserve a minimum heart rate.

In some embodiments, once an event is detected, the process characterizes the detected event, if necessary, and controls pacing, as appropriate, based on the detection. Thus, the process may re-enter the main loop at, for example, block 420.

If the extended time period expires, the stimulation device may pace the heart as necessary (block 616). For example, the process may return to block 424 in the main loop. It should be appreciated that the above description is provided as an example. Thus, other criteria may be used to define when a mode switch should or may occur.

Figure 7:
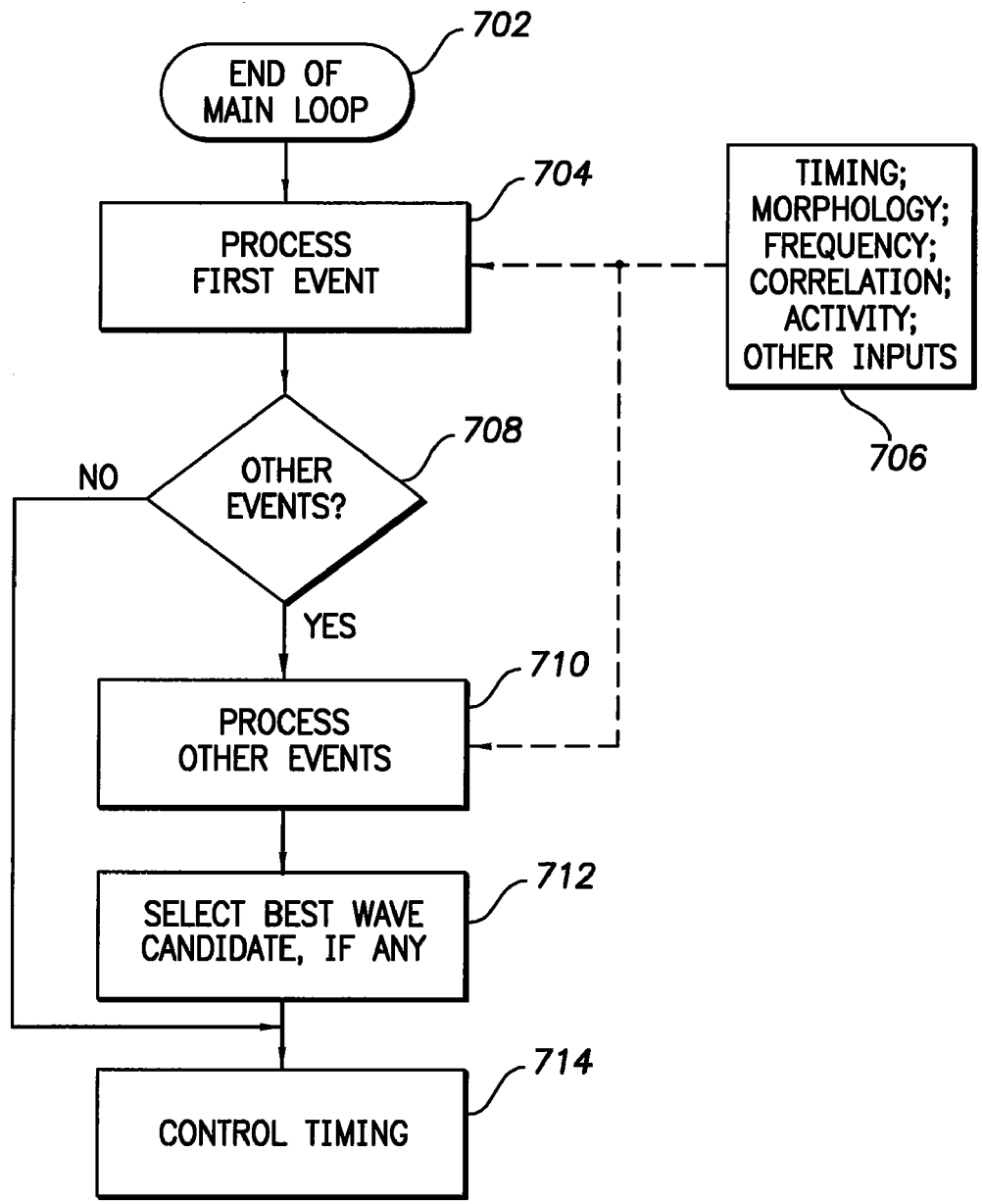
FIG. 7 is a simplified flow chart of one embodiment of characterization operations that may be performed in accordance with the invention.

FIG. 7 is simplified flowchart illustrating one embodiment of retrospective detection operations that may be performed when at least one event has been sensed. As represented by block 702, these operations may correspond to, for example, the operations associated with one or more of the blocks 414, 418 and 420 in FIG. 4.

At block 704, the process evaluates the first sensed event. As discussed above, this processing may be performed any time after the event has been sensed or detected. For example, the event information may be processed in real-time and/or may be stored in a data memory for subsequent processing. In some embodiments, the first detected event may be preliminarily characterized as a candidate for a particular type of wave. For example, if the first event is detected by a threshold detector in an atrial channel, the event may be characterized as a candidate P-wave. Subsequent processing of the event and, optionally other events, may determine whether the candidate P-wave is to be characterized as a true P-wave.

In some embodiments the first event may be used to trigger a retrospective detection interval. For example, a real-time detection mode (e.g., threshold-based) may be used to detect the first event. The detection mode may then be changed to perform retrospective detection during a time period such that signals from one or more input channels are collected and analyzed to determine whether an event has been detected and, if so, the type of event. This triggered detection window may be terminated, for example, by the end of an escape interval, by other criteria described herein or by still other criteria.

In some embodiments processing the first event may involve processing the first sensed event in its entirety. For example, the entire waveform associated with a received signal (e.g., a P-wave) may be processed to characterize the event. Such an operation is in contrast with conventional threshold detection schemes where a decision as to the type of wave may be made after only a portion of the signal (e.g., a portion of the leading edge) is received. The retrospective detection method thus facilitates a more accurate analysis of the first detected event.

As represented by block 706 and the associated dashed line, the processing may utilize signals and/or data that is derived from other sensed inputs, stored in data memory or obtained from other sources. These signals/data may include, for example, morphology data, timing data, activity signals, other signal/data discussed herein or other signals/data that may be used to characterize sensed events.

As represented by blocks 708-712, the process evaluates any other sensed events. This processing may be performed any time after an event has been sensed and may involve, for example, processing operations as discussed above in conjunction with block 704. At this point in the process all of the received events may be characterized as, for example, certain types of waves, candidate waves or noise.

At block 712, if more than one candidate wave of a particular type was detected, the process may select one of the candidates to be characterized as the true wave. This process may involve, for example, comparing the characteristics of the events with each other and/other known or expected data. This process also may involve comparing the timing of one or more of the events, other known events and expected events. For example, both a near and a far-field R-wave detection followed by both a near and a far-field T-wave detection during an alert period may serve as a better indication of a premature ventricular contraction ("PVC") than a ventricular threshold detection alone.

At block 714 the process controls the cardiac timing based on the characterized event(s). This process may involve, for example, changing or maintain the timing intervals or altering pacing.

Figure 8:
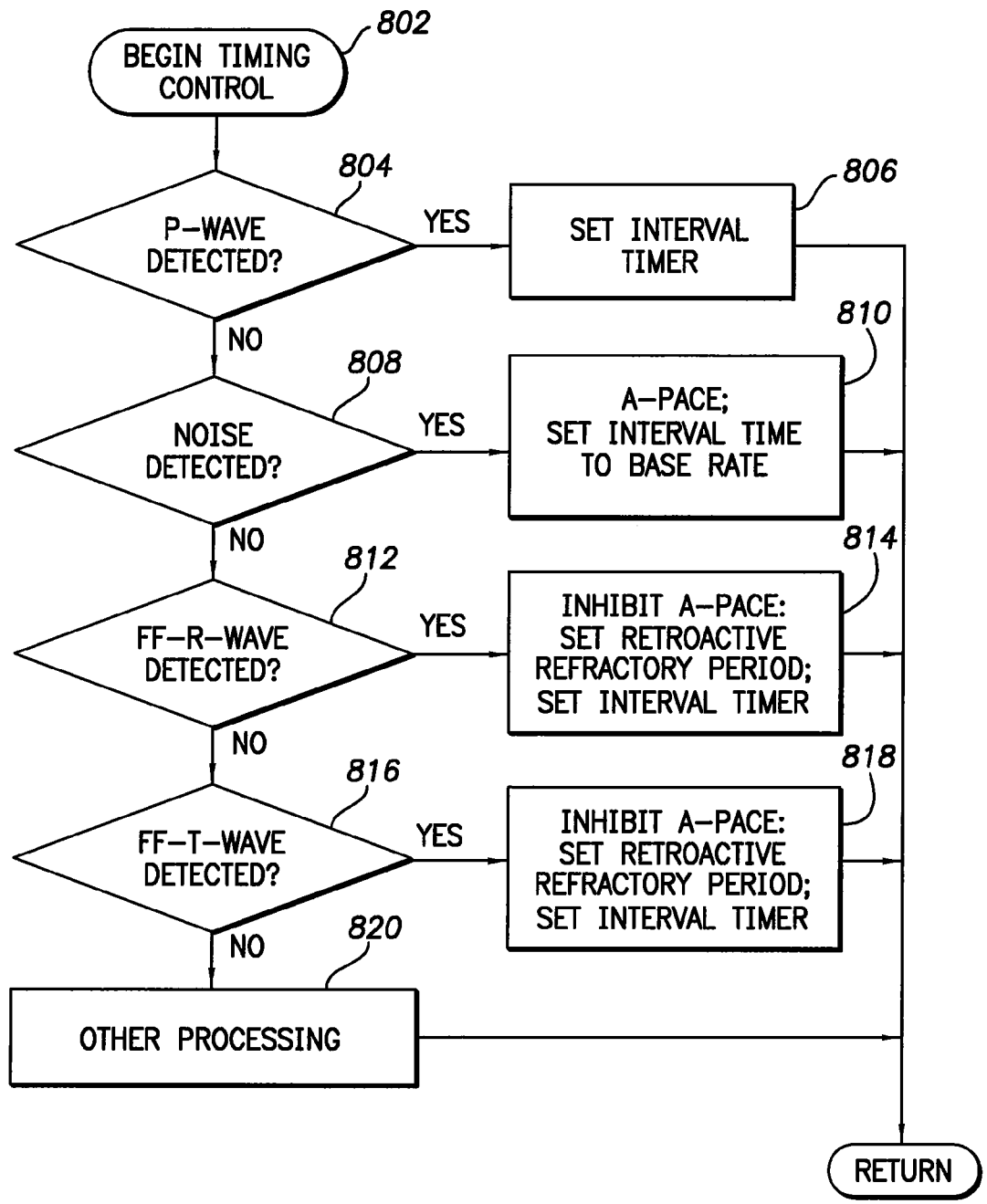
FIG. 8 is a simplified flow chart of one embodiment of pacing control operations that may be performed in accordance with the invention.

One embodiment of a timing control process is discussed in conjunction with FIG. 8. As represented by block 802, the simplified flowchart of FIG. 8 may correspond to some or all of the timing control operations discussed herein, for example, at blocks 420 or 714.

The process of FIG. 8 may be better understood by reference to the timing diagrams of FIGS. 9-12. For example, these timing diagrams show how the timing intervals may be maintained or adjusted, depending on the received signals.

Figure 9:
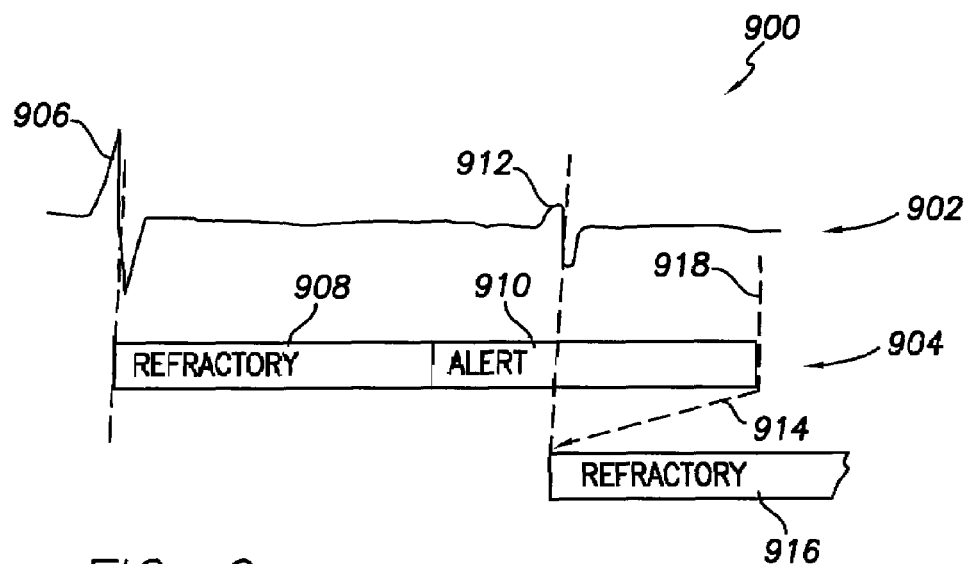
FIG. 9 is a simplified diagram illustrating one embodiment of retrospective detection timing that may be provided in accordance with the invention.
Figure 10:
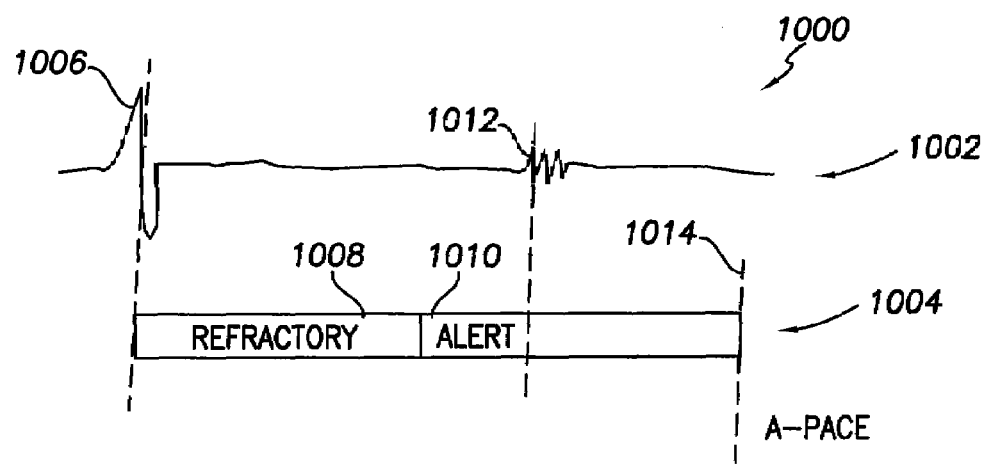
FIG. 10 is a simplified diagram illustrating one embodiment of retrospective detection timing that may be provided in accordance with the invention.

The timing diagrams of FIGS. 9-10 illustrate one embodiment where retrospective detection is applied to an atrial channel. It should be appreciated, however, that similar principles may apply when retrospective detection is applied to other channels (e.g., the other atrial channel, the ventricle channel(s), etc.)

At block 804, when a P-wave is detected, the process sets the interval timing so that cardiac signals are sensed and, if necessary, generated, based on the timing of the P-wave (block 806). One example of this process is depicted in the simplified timing diagram 900 of FIG. 9. A simplified timing diagram 902 represents a sensed signal (e.g., an IEGM) where amplitude is represented by the y-axis and time is represented by the x-axis. A second simplified timing diagram 904 represents various timing intervals that may be defined for the heart cycle.

A wave 906 represents a sensed R-wave or a ventricle pace. A refractory period 908 follows the wave 906. The refractory period 908 may be on the order of, for example, 400 mS. An alert period 910 follows the refractory period 908. The alert period 910 may be on the order of, for example, 457 mS. When a signal 912 is sensed in the atrial channel during the alert period 910, the process does not immediately identify the signal 912 as a P-wave. Instead, as discussed herein, sensing (and processing) may continue until the end of the alert period 910, as represented by a dashed line 918. If the signal 912 is characterized as a P-wave at the end 918 of the alert period 910 then, as represented by a dashed line 914, the interval timing is adjusted such that a refractory period 916 for the atrial channel is defined to start at a time that coincides with the signal 912.

Adjusting a timing interval may be accomplished in a variety of ways. For example, in some embodiments a counter may be set or reset. In some embodiments the current value of a counter may be modified. In some embodiments the value in a counter designating the current time may be modified to reflect that the beginning of a time interval (e.g., P-wave detection) is a certain amount of time in the past.

Referring again to FIG. 8, at block 808 a sensed event may be characterized as noise. In this case, the process may pace the atrium when a P-wave is not sensed before the atrial escape interval elapses. The process also may set the interval timing to the base rate (block 810).

One example of this process is depicted in a simplified timing diagram 1000 of FIG. 10. FIG. 10 also includes a simplified timing diagram 1002 representing a sensed signal and a second simplified timing diagram 1004 representing various timing intervals. A wave 1006 represents a sensed R-wave or a ventricle pace. A refractory period 1008 and an alert period 1010 follow the wave 1006. When a signal 1012 is sensed in the atrial channel during the alert period 1010, the process continues sensing (and processing) until the end of the alert period 1010 as represented by a dashed line 1014. If the signal 1012 is characterized as noise at the end 1014 of the alert period 1010 and no P-wave is sensed (as depicted in FIG. 10), the process paces the atrium (A-Pace) and resets the rate timer to the base rate.

At block 812 in FIG. 8, when the sensed event is characterized as a far-field R-wave, the process inhibits pacing in the atrium, retrospectively sets the refractory period and sets the interval timer (block 814).

Figure 11:
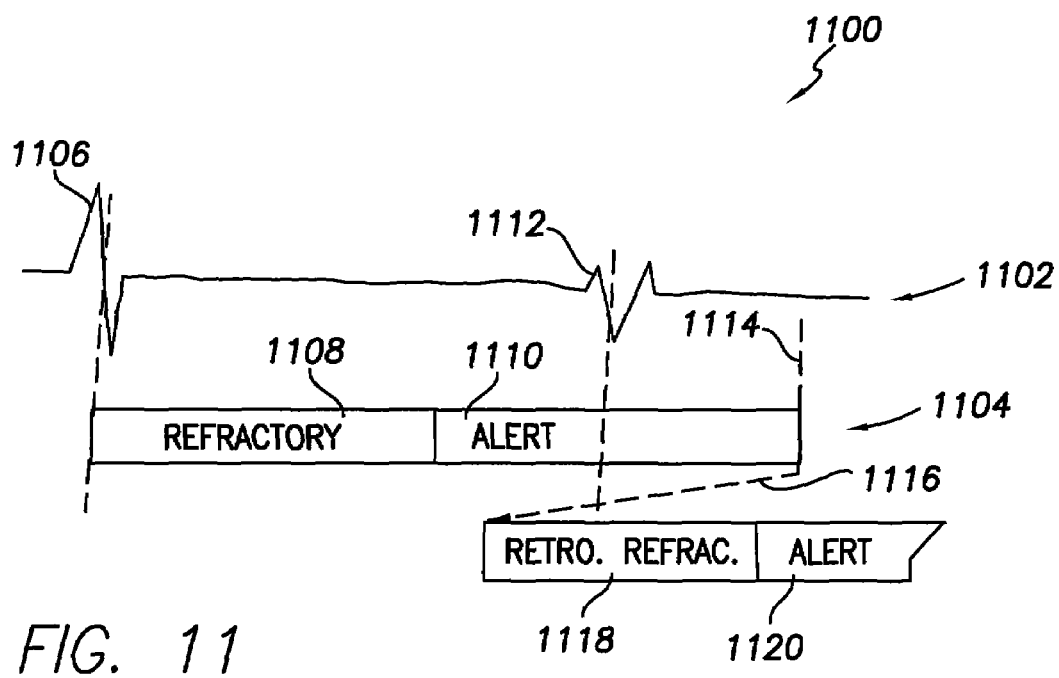
FIG. 11 is a simplified diagram illustrating one embodiment of retrospective detection timing that may be provided in accordance with the invention.

One example of this process is depicted in a simplified timing diagram 1100 of FIG. 11. FIG. 11 also includes a simplified timing diagram 1102 representing a sensed signal and a second simplified timing diagram 1104 representing various timing intervals. A wave 1106 represents a sensed R-wave or a ventricle pace. A refractory period 1108 and an alert period 1110 follow the wave 1106. When a signal 1112 is sensed in the atrial channel during the alert period 1110, the process continues sensing (and processing) until the end of the alert period 1110, as represented by a dashed line 1114. If the signal 1112 is characterized as a far-field R-wave at the end 1114 of the alert period 1110 then, as represented by a dashed line 1116, the interval timing is adjusted such that a retrospective refractory period 1118 for the atrial channel is defined to start a given period of time (offset) before the signal 1112 was sensed. For example, the offset may be defined as the atrium to ventricle ("A-V") conduction time. This interval may be, for example, on the order of 125 mS. In other words, the refractory period 1118 is defined to begin at a time that approximately coincides with the time at which the P-wave should have occurred. The other cardiac timing intervals (e.g., alert period 1120) are thus adjusted accordingly.

At block 816 in FIG. 8, when the sensed event is characterized as a far-field T-wave, the process inhibits pacing in the atrium, retrospectively sets the refractory period and sets the interval timer (block 818).

Figure 12:
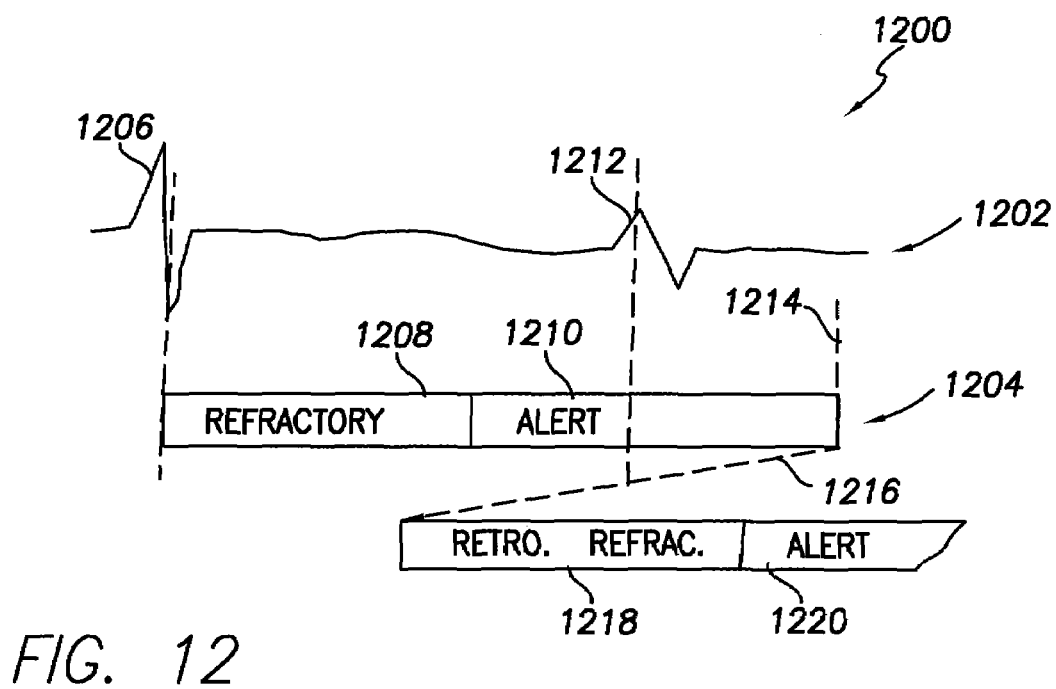
FIG. 12 is a simplified diagram illustrating one embodiment of retrospective detection timing that may be provided in accordance with the invention.

One example of this process is depicted in a simplified timing diagram 1200 of FIG. 12. FIG. 12 also includes a simplified timing diagram 1202 representing a sensed signal and a second simplified timing diagram 1204 representing various timing intervals. A wave 1206 represents a sensed R-wave or a ventricle pace. A refractory period 1208 and an alert period 1210 follow the wave 1206. When a signal 1212 is sensed in the atrial channel during the alert period 1210, the process continues sensing (and processing) until the end of the alert period 1210, as represented by a dashed line 1214. If the signal 1212 is characterized as a far-field T-wave at the end 1214 of the alert period 1210 then, as represented by a dashed line 1216, the interval timing is adjusted such that a retrospective refractory period 1218 for the atrial channel is defined to start a given period of time (offset) before the signal 1212 was sensed. For example, the offset may be defined as the A-V conduction time plus the R-wave to T-wave ("RT") interval. The RT interval may be, for example, on the order of 200 mS. Thus, the offset may be on the order of 325 mS. Again, the refractory period 1218 is defined to begin at a time that approximately coincides with the time at which the P-wave should have occurred. The other cardiac timing intervals (e.g., alert period 1220) are adjusted accordingly.

As represented by block 820 in FIG. 8, other processing may be performed when an event is characterized in some other manner. After the timing control operations are completed, processing may then return to, for example, block 402 in FIG. 4.

It should be appreciated that the various components described herein may be incorporated in a device independently of the other components. For example, a device incorporating the teachings herein may include various combinations of these components. Thus, not all of the components described herein may be employed in every such device.

Different embodiments of the stimulation device may include a variety of hardware and software processing components. In some embodiments, hardware components such as processors, controllers, state machines and/or logic may be used to implement the described components or circuits. In some embodiments, code such as software or firmware executing on one or more processing devices may be used to implement one or more of the described operations or components.

The components and functions described herein may be connected/coupled in many different ways. The manner in which this is done may depend, in part, on whether and how the components are separated from the other components. In some embodiments some of the connections/couplings represented by the lead lines in the drawings may be in an integrated circuit, on a circuit board or implemented as discrete wires.

The signals discussed herein may take several forms. For example, in some embodiments a signal may be an electrical signal transmitted over a wire, optical signals transmitted over and optical medium such as fiber, or wireless signals transmitted through space. In addition, a group of signals may be collectively referred to as a signal herein. The signals discussed above also may take the form of data. For example, in some embodiments an application program may send a signal to another application program. Such a signal may be stored in a data memory.

In summary, the invention described herein generally relates to an improved cardiac stimulation apparatus and method. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of detecting a cardiac event comprising:
    detecting a first event in at least one cardiac channel during a cardiac cycle;
    after the first event has been detected and before an end of an escape interval associated with the cardiac cycle, sensing for at least one other event in another cardiac channel; and
    performing retrospective detection of the first event near the end of the escape interval, wherein the retrospective detection comprises identifying a type of the first event based on the sensing in the another cardiac channel.

2. The method of claim 1 comprising continuing the sensing in the another cardiac channel beyond the end of the escape interval to identify a type of an event sensed on the another cardiac channel near the end of the escape interval.

3. The method of claim 1 comprising switching, based on the sensing in the another cardiac channel, from a retrospective mode of detection to a real-time mode of detection near the end of the escape interval.

4. The method of claim 1 comprising controlling cardiac pacing in accordance with the retrospective detection.

5. The method of claim 4 wherein the at least one cardiac channel is an atrial channel and the first event is tentatively identified as a P-wave upon detection.

6. The method of claim 5 wherein the sensing for at least one other event in another cardiac channel comprises sensing for far-field signals that originate in a ventricle.

7. The method of claim 5 comprising sensing a non-cardiac channel, wherein the retrospective detection comprises identify a type of the first event based on the sensing in the non-cardiac channel.

8. A method of controlling cardiac pacing comprising:
    detecting a first atrial waveform in at least one atrial channel during a cardiac cycle;

upon detection of the first atrial waveform, sensing in the at least one atrial channel for a time period to detect any other atrial waveforms, wherein the time period terminates before an end of an escape interval associated with the cardiac cycle;

processing the first detected atrial waveform and any other atrial waveforms that were detected to identify a type of the first atrial waveform, wherein the processing is performed near the end of the escape interval; and controlling pacing in accordance with the identified atrial waveform.

9. The method of claim 8 comprising continuing to sense in the at least one atrial channel beyond the end of the escape interval to identify a type of a second atrial waveform detected near the end of the time period.

10. The method of claim 8 comprising changing from a retrospective mode of detection to a real-time mode of detection near the end of the time period based on the sensing in the at least one atrial channel.

11. The method of claim 6 wherein, upon detection, the first atrial waveform is tentatively identified as a candidate P-wave.

12. The method of claim 11 wherein, as a result of the processing, the first atrial waveform is subsequently identified as not being a P-wave.

13. The method of claim 8 comprising applying a retrospective refractory period if the first atrial waveform is identified as a far-field R-wave or a far-field T-wave.

14. An implantable cardiac stimulation apparatus comprising:

at least one cardiac sense circuit configured to sense signals in at least one atrium;

a real-time detector configured to detect a first atrial waveform during a cardiac cycle based on the sensing;

at least one data collection circuit configured to collect data associated with the first atrial waveform and any other atrial waveforms sensed by the at least one cardiac sense circuit during a time period, wherein the time period terminates before an end of an escape interval associated with the cardiac cycle;

at least one signal processor configured to process the collected data to identify a type of the first atrial waveform; and at least one timing circuit configured to control cardiac pacing on a beat-by-beat basis by defining at least one cardiac pacing interval in accordance with the identified atrial waveform.

15. The apparatus of claim 14 wherein the at least one cardiac sense circuit is configured to sense waveforms from a left atrium and a right atrium.

16. The apparatus of claim 14 wherein the at least one signal processor comprises at least one of the group consisting of a timing processor, a morphology processor, a correlation processor, and a frequency processor.

17. The apparatus of claim 14 wherein the at least one data collection circuit is configured to collect data beyond the end of the escape interval to identify a type of a second atrial waveform detected near the end of the time period.

18. The apparatus of claim 14 wherein the at least one signal processor is configured to invoke, based on the collected data, a change from a retrospective mode of detection to a real-time mode of detection near the end of the time period.

19. The apparatus of claim 14 wherein:

the real-time detector is configured to tentatively identify a type of the first atrial waveform as a candidate P-wave; and the at least one signal processor is configured to subsequently identify a type of the first atrial waveform as not being a P-wave based on the collected data.

20. The apparatus of claim 14 wherein the at least one timing circuit is configured to apply a retrospective refractory period if the first atrial waveform is identified as a far-field R-wave or a far-field T-wave.

* * * * *